United States Patent
Ehlers et al.

(10) Patent No.: US 9,299,139 B2
(45) Date of Patent: Mar. 29, 2016

(54) VOLUMETRIC ANALYSIS OF PATHOLOGIES

(71) Applicant: THE CLEVELAND CLINIC FOUNDATION, Cleveland, OH (US)

(72) Inventors: Justis P. Ehlers, Shaker Hts., OH (US); David Xu, Cleveland, OH (US); Peter K. Kaiser, Shaker Hts., OH (US); William J. Dupps, Bay Village, OH (US); Sunil K. Srivastava, Shaker Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 124 days.

(21) Appl. No.: 13/850,846

(22) Filed: Mar. 26, 2013

(65) Prior Publication Data

US 2014/0119624 A1    May 1, 2014

Related U.S. Application Data

(60) Provisional application No. 61/615,656, filed on Mar. 26, 2012.

(51) Int. Cl.
*G06T 7/00*   (2006.01)
*A61B 6/03*   (2006.01)
(Continued)

(52) U.S. Cl.
CPC ............ *G06T 7/0012* (2013.01); *A61B 5/0066* (2013.01); *G06T 7/0016* (2013.01); *G06T 7/0081* (2013.01); *G06T 7/0083* (2013.01);
(Continued)

(58) Field of Classification Search
None
See application file for complete search history.

(56) References Cited

U.S. PATENT DOCUMENTS 6,728,334 B1    4/2004   Zhao
6,842,638 B1 *  1/2005   Suri et al. .................. 600/425
(Continued)

FOREIGN PATENT DOCUMENTS

| WO | 2012/027849 A1 | 3/2012 |
| WO | 2012100030 A2 | 7/2012 |
| WO | 2012/126070 A1 | 9/2012 |

OTHER PUBLICATIONS

Hu, Multimodal 3-D Segmentation of Optic Nerve Head Structures From Spectral Domain OCT Volumes and Color Fundus Photographs, Dec. 2011. Doctorate Thesis for Electrical and Computer Engineering Department of Univeristy of Iowa. 146 pages.*

(Continued)

*Primary Examiner* — Utpal Shah
*Assistant Examiner* — Mai Tran
(74) *Attorney, Agent, or Firm* — Tarolli, Sundheim, Covell & Tummino LLP

(57) ABSTRACT

Systems and methods are provided for volumetric analysis of pathologies. A segmentation component is configured to determine, for each of a series of images of a region of interest containing a pathological feature, a set of segmentation boundaries within the image representing a cross-section of the pathological feature. A mesh generation component is configured to link the sets of segmentation boundaries from adjacent images in the series of images to generate a polygonal mesh representing a volumetric reconstruction of the pathological feature. A volumetric measurement component is configured to calculate volumetric parameters from the volumetric reconstruction representing the pathological feature. A user interface is configured to provide the calculated volumetric parameters to an associated display.

17 Claims, 2 Drawing Sheets

(51) Int. Cl.
*A61B 5/00* (2006.01)
*G06T 7/60* (2006.01)
*G06T 17/20* (2006.01)

(52) U.S. Cl.
CPC .............. *G06T 7/0093* (2013.01); *G06T 7/602* (2013.01); *G06T 17/20* (2013.01); *G06T 2207/10101* (2013.01); *G06T 2207/20016* (2013.01); *G06T 2207/20072* (2013.01); *G06T 2207/30041* (2013.01)

(56) References Cited

U.S. PATENT DOCUMENTS

| | | | |
|---|---|---|---|
| 7,937,132 B2* | 5/2011 | Piron et al. | 600/415 |
| 8,165,385 B2 | 4/2012 | Reeves et al. | |
| 2004/0068187 A1* | 4/2004 | Krause et al. | 600/443 |
| 2006/0058592 A1 | 3/2006 | Bouma et al. | |
| 2007/0058865 A1* | 3/2007 | Li et al. | G06K 9/4638 382/173 |
| 2008/0037845 A1* | 2/2008 | Deuerling-Zheng et al. | 382/130 |
| 2010/0113887 A1* | 5/2010 | Kalafut et al. | 600/300 |
| 2011/0013837 A1 | 1/2011 | Bergman et al. | |
| 2011/0235882 A1* | 9/2011 | Van Wijk | 382/131 |
| 2011/0268328 A1* | 11/2011 | Bar-Aviv et al. | 382/128 |

OTHER PUBLICATIONS

Wang et al., "Semiautomatic segmentation and quantification of calcified plaques in intracoronary optical coherence tomography images", Journal of Biomedical Optics, 2010, vol. 15, No. 6, pp. 061711-1: 061711-10.
PCT International Search Report and Written Opinion, mailed Oct. 25, 2013, pp. 1-15.
Zawadzki, et al. Improved Representation . . . Reconstruction, Vision Science and Advanced Retinal . . . Lab., pp. 1-8.

* cited by examiner

US 9,299,139 B2

VOLUMETRIC ANALYSIS OF PATHOLOGIES

RELATED APPLICATIONS

The present application claims priority to U.S. Provisional Patent Application Ser. No. 61/615,656 filed Mar. 26, 2012 entitled AUTOMATED VOLUMETRIC IMAGE ANALYSIS OF PATHOLOGICAL CONDITIONS IN THE CLINICAL AND SURGICAL SETTINGS, the entire contents of which being incorporated herein by reference in its entirety for all purposes.

TECHNICAL FIELD

The present invention relates generally to the field of medical imaging, and more particularly to volumetric analysis of pathological features in a series of consecutive images.

BACKGROUND OF THE INVENTION

Optical coherence tomography (OCT) is an optical signal acquisition and processing method that captures micrometer-resolution, three-dimensional images from within optical scattering media, such as biological tissue. Optical coherence tomography is an interferometric technique, typically employing near-infrared light. The use of relatively long wavelength light allows it to penetrate into the scattering medium. Depending on the properties of the light source, optical coherence tomography has achieved sub-micrometer resolution. Optical coherence tomography systems are employed in diverse applications, including art conservation and diagnostic medicine, notably in ophthalmology where it can be used to obtain detailed images from within the retina and other ophthalmic tissues (e.g., cornea).

SUMMARY OF THE INVENTION

In accordance with an aspect of the present invention, a non-transitory computer readable medium stores executable instructions that include a coarse segmentation component configured to determine, for each of a series of B-scan images, a set of constraint boundaries, based on natural contours within a region of tissue, from an optical coherence tomography (OCT) B-scan image. The coarse segmentation component truncates all image area outside of the constraint boundaries to provide a truncated image. A fine segmentation component is configured to determine, for each truncated image, a set of pathology boundaries within the truncated image representing a cross-section of the pathological feature. A mesh generation component is configured to link the sets of pathology boundaries from adjacent images in the series of B-scan images to generate a polygonal mesh representing the volumetric reconstruction of the pathological feature. A user interface is configured to provide the polygonal mesh to an associated display.

In accordance with another aspect of the present invention, a non-transitory computer readable medium stores executable instructions that include a segmentation component configured to determine, for each of a series of images of a region of interest containing a pathological feature, a set of segmentation boundaries within the image representing a cross-section of the pathological feature. A mesh generation component is configured to link the sets of segmentation boundaries from adjacent images in the series of images to generate a polygonal mesh representing a volumetric reconstruction of the pathological feature. A volumetric measurement component is configured to calculate volumetric parameters from the volumetric reconstruction representing the pathological feature. A user interface is configured to provide the calculated volumetric parameters to an associated display.

In accordance with yet another aspect of the present invention, a method is provided for volumetric analysis of a pathological feature. A region of interest containing a pathological feature is imaged with an associated imager prior to a start of a therapeutic intervention to provide a set of pre-intervention scan data. A first value of a volumetric parameter is calculated from the set of pre-intervention scan data. The region of interest is imaged with the imager after the start of the therapeutic intervention to provide a set of post-intervention scan data. A second value of the volumetric parameter is calculated from the set of post-intervention scan data. A clinical outcome associated with the therapeutic intervention is predicted from at least a function of the first value of the volumetric parameter and the second value of the volumetric parameter. The predicted clinical outcome is displayed to a user at an associated output device.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
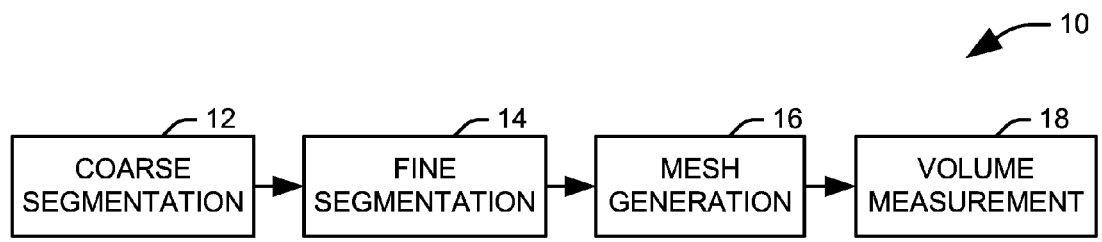
FIG. 1 illustrates a functional block diagram of a system for locating pathological features within a series of OCT B-scans in accordance with an aspect of the present invention.

FIG. 1 illustrates a functional block diagram of a system 10 for locating pathological features within a series of OCT B-scans in accordance with an aspect of the present invention. It will be appreciated that the system 10 can be implemented as dedicated hardware, machine executable instructions stored on a non-transitory computer readable medium and executed by an associated processor, referred to herein as software, or some combination of dedicated hardware and software components. It will be appreciated that the system 10 can be implemented as a standalone system working in conjunction with an OCT scanner or as an integral part of an OCT scanner.

The system 10 includes an imager interface 12 configured to receive B-scan data from an associated scanning assembly, and optionally three-dimensional volume data, and video data from clinical, research, and/or intraoperative imaging that can be imported and analyzed on a frame-by-frame basis. In accordance with an aspect of the present invention, the B-scan data can include a series of B-scan images representing contiguous regions of eye tissue, such that the images collectively represent a volume of eye tissue. The images are provided to a coarse segmentation component 12 configured to determine, for each of a series of B-scan images, a set of constraint boundaries, based on natural contours within a region of eye tissue, from an optical coherence tomography (OCT) B-scan image and truncate all image area outside of the constraint boundaries to provide a truncated image. For example, if a pathological feature of interest has been determined to lie within a particular layer or set of layers of the retina or generally occurs within a set of layers, the coarse segmentation component 12 can identify the specific layers and truncate the image to include only those layers within the image.

The truncated images are then provided to a fine segmentation component 14 configured to determine, for each truncated image, a set of pathology boundaries within the truncated image representing a pathological feature. It will be appreciated that this segmentation can be performed using any appropriate segmentation algorithm. In one implementation, the segmentation is performed by solving a maximum-flow minimum-cut problem, defined according to image intensity and gradient cues within the image, using an appropriate optimization algorithm. In accordance with an aspect of the present invention, the results of each image can be used as weights in the segmentation of a succeeding image in the series. Since it is unlikely that the contour of a given pathological feature will be wildly discontinuous, pixels near the location corresponding to the segmentation boundary of the adjacent image can be favored in the segmentation via adjustment of their weights or cost values.

The segmentation boundaries from the plurality of images are provided to a mesh generation component 16. The mesh generation component 16 creates a three-dimensional polygonal mesh, representing the pathological feature, from the segmentation boundaries extracted from each image. For example, representative points can be selected on each segmentation boundary, and the representative points on adjacent boundaries can be joined to form a volumetric reconstruction. The generated volumetric reconstruction is then provided to a volume measurement component 18 configured to calculate one or more volumetric parameters from the generated volumetric reconstruction. The specific volumetric parameters to be calculated can vary with the disorder and can include, for example, a total volume, a base area, a top area, a maximal base width, and a minimum width (e.g., of a full thickness macular hole). Each of the generated volume, the calculated volumetric parameters, and the B-scan slices can be displayed to a user at an associated user interface (not shown).

Figure 2:
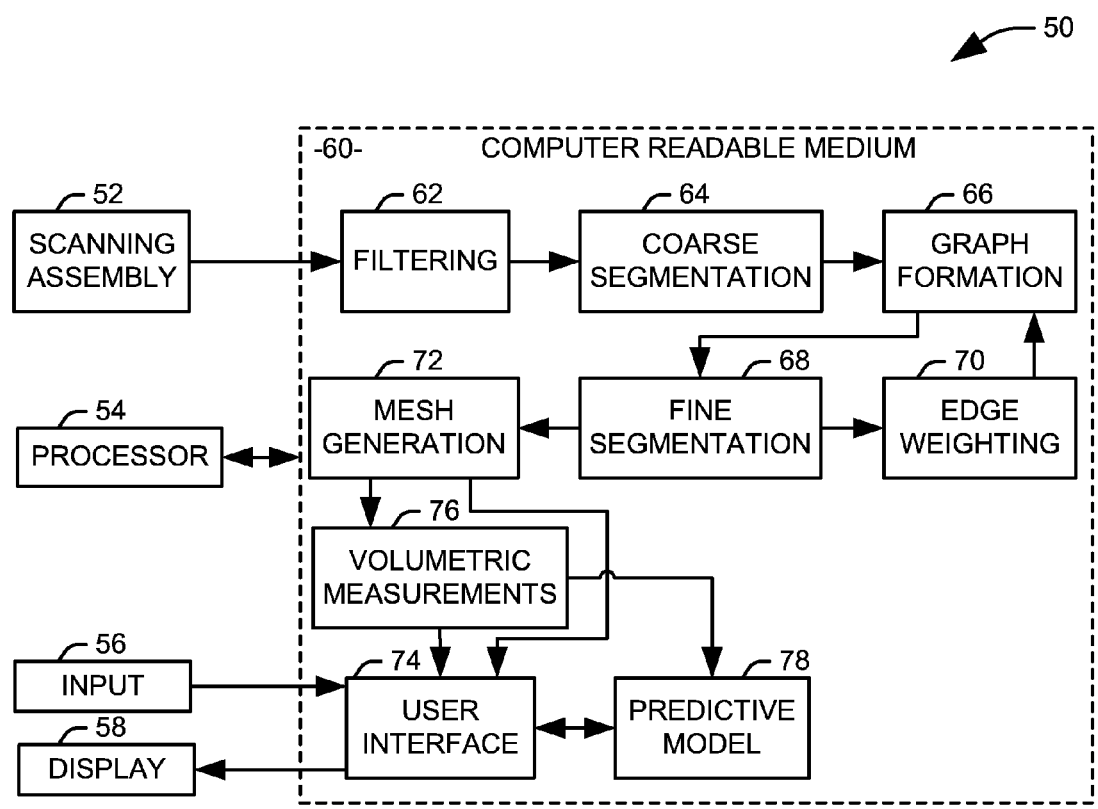
FIG. 2 illustrates one implementation of a system for locating pathological features within a series of OCT B-scans in accordance with an aspect of the present invention.

FIG. 2 illustrates one implementation of a system 50 for locating pathological features within a series of OCT B-scans in accordance with an aspect of the present invention. The system 50 provides robustness against variability in OCT scan quality, scan parameters, OCT scanning devices, OCT light source, OCT acquisition technique, the automated nature by which it works, and the ability to extract near limitless clinically and research-specific parameters. An OCT scanning assembly 52 provides OCT B-scan data to an image analysis component implemented as a general purpose processor 54 operatively connected to a non-transitory computer readable medium 60 storing machine executable instructions. An input device 56, such as a mouse or a keyboard, is provided to allow a user to interact with the system, and a display 58 is provided to display imaging data and calculated parameters to the user.

The machine executable instructions include a filtering component 62 that conditions the received B-scan images for further analysis. In one implementation, image smoothing is performed at the filtering component using a Gaussian convolution window to attenuate noise. A coarse segmentation component 64 performs an automated delineation of a set of constraint boundaries for each image based on natural contours of the retinal, choroidal, or anterior segment topology. Selection of the contours used is dependent on the field of view within the eye. These boundaries serve to constrain the search window, set natural limits on the spatial extent of pathologic features, normalize the image for variations in patient anatomy including shape, curvature, and size, and provide landmarks for volumetric analysis.

In the illustrated implementation, contour boundaries are delineated by local image intensity, gradient, and contrast cues that are determined from immediate pixel neighbors and local regional properties. An optimal segmentation of boundaries is performed via a sparse maximum-flow minimum-cut graph search on a planar, four-connected graph representation of the weighted contributions of pixel intensity, pixel gradient, and/or shape/location cues from adjacent frames on a multi-frame image stack. The result of the maximum-flow minimum-cut analysis identifies the globally optimal boundary with greatest image intensity or image gradient. For example, the natural topological constraints in retinal/posterior segment images can be the boundaries of the internal limiting membrane and the retinal pigment epithelium (RPE). In anterior segment images, the natural topological constraints can be the anterior epithelial surface, the posterior endothelial surface, and the epithelial to Bowman's membrane interface.

The constraint boundary determination at the coarse segmentation component 64 is performed with pixel-level accuracy. This allows the option of using the identified constraint boundaries as the final segmentation of interest, such as in the determination of width, height, thickness, area, volume, or other geometry of the total retinal, choroidal, optic nerve, angle, iris, or cornea/corneal sublayers. For example, the constraint boundary identification enables the measurement of corneal volume and curvature, central/peripheral corneal thickness, corneal epithelial and stroma thickness and volume, retinal area or volume in pathologic states, including epiretinal membrane (ERM) and vitreomacular traction (VMT), choroidal area or volume in central serous chorioretinopathy, uveitic conditions, age-related macular degeneration, and other pathologies. The coarse segmentation component 64 also allows a user to provide an operator-assisted determination of constraint boundaries via the input device 56 in the event of an automated boundary detection failure or if it is desirable to select specific pathologic structures of interest. Once the constraint boundaries are determined, the coarse segmentation component truncates the image to remove the image area outside of the constraint boundary, decreasing the computation time of subsequent segmentation routines.

Segmentation of pathologic features is performed within the constraint boundary at a graph formation component 66, a fine segmentation component 68, and an edge weighing component 70. In the illustrated implementation, the graph formation component 66 generates an undirected graph with vertices representing image pixels and eight-connected edges having weights representing a cost generated from image gradient and neighborhood similarity metrics. Additionally, each pixel has an edge to two common vertices, denoted the source and sink vertex, with weights representing a cost determined from of pixel intensity and regional histogram similarity metrics.

The network of edge weights forms an energy minimization problem based on the costs of image intensity and gradient/boundary cues. The fine segmentation component 68 determines a cut through the graph is as a removal of a set of edges sufficient to separate the source and sink vertices. The fine segmentation component 68 solves the maximum-flow, minimum-cut problem in a single-source single-sink network to find the set of edges, which performs an energy minimization of edge costs and derives the globally optimal bipartition of the image into one or more features and background. This formulation is used to segment pathologic ocular structures by encoding edge weights according to an associated image gradient and/or neighborhood similarity metrics (i.e., a parameter representing the similarity of pixels connected to a given pixel associated with the edge) as well as a priori estimates of the pixel intensity and histogram distributions of pathologic structures. The solution of the maximum-flow minimum-cut problem is the optimal segmentation of the pathologic feature based on the aforementioned energy minimization.

In the illustrated implementation, segmentation is performed on a frame-by-frame basis, with frames processed sequentially according to their spatial ordering. The segmentation boundary in an adjacent frame is used by the edge weighting component 70 to reweight edges on the current frame to produce a linearly decreasing cost function as the edges approaches the adjacent segmentation. Accordingly, the segmentation in each new frame can be guided by the results of previous frames to provide a continuous boundary for the pathological features. Adjacent frames are then combined at a mesh generation component 72 to generate a three-dimensional polygonal mesh from the set of boundaries of interest for a given application. Depending on the specific pathology feature being examined, the boundaries can include either or both the segmentation boundaries produced at the fine segmentation component 68 and the constraint boundaries produced at the coarse segmentation component 64. The generated polygonal mesh volumes can be provided to a user interface 74 to be accessible to a user at the display 58.

Specifically, the segmentation boundaries from the fine segmentation component 68 can be performed on OCT images of full-thickness macular holes, macular pseudoholes, lamellar holes, vitreomacular adhesion, cystoid macular edema, subretinal fluid, sub RPE fluid, intra-RPE fluid, VMT, ERM, and choroidal thickness in the posterior segment. In the cornea, the fine segmentation component 68 performs an automated segmentation of interfaces between fluid and tissue, air and tissue, and fluid and air, including interfaces in the lamellar interface of Descemet's Stripping Endothelial Keratoplasty (DSAEK).

Once appropriate volumes have been established, a plurality of volumetric parameters can be calculated form the polygonal mesh volumes at a volumetric measurement component 76. The specific volumetric parameters to be calculated can vary with the application and can include, for example, a total volume, a base area, a top area, a maximal base width, and a minimum width (e.g., of a full thickness macular hole). In other applications, measurements of parameters describing epithelial, stromal, substromal compartments separated by a tissue interface (such as LASIK flaps, DSAEK grafts, anterior lamellar keratoplasty grafts) can be made from a volume representing fine segmentation boundaries. The volumetric parameters can also include total corneal geometry measurements, including volumes for each of these layers. In the anterior segment, the volumetric parameters can include angle geometry measurements, iris thickness and configuration measurements, and anterior segment mass evaluation, including area and volume. The calculated parameters can be provided to the user interface 74 for display to a user.

The calculated volumetric parameters can also be provided to a predictive model 78 configure to evaluate a clinical outcome for a patient according to at least the calculated volumetric parameters. It will be appreciated, of course, that the predictive model may also use other predictors associated with the patient, including categorical predictors, such as predictors representing medical history and the presence or absence of various conditions, as well as integral or ratio parameters, such as age, blood glucose level, or similar parameters. The predictive model 74 can include one or more appropriate supervised learning algorithms, such as regression models, artificial neural networks, support vector machines, and statistical classifiers that predict a clinical outcome using the calculated volumetric parameters as predictors in the model. The predictive model 78 can be used to provide decision support for a physician in conducting a therapeutic intervention by recommending one or more parameters for the intervention itself or for post-intervention care. For example, volumetric measurements of macular holes can be provided to the predictive model to determine a minimum period for which the patient must maintain a prone position.

In accordance with an aspect of the present invention, the predictive model 78 can predict one or more clinical outcomes as a function of a first volumetric measurement, derived from OCT scans taken prior to the therapeutic intervention, and a second volumetric measurement, derived from OCT scans taken during or immediately after the intervention. In one example, the function is a weighted linear combination of the two values, although it will be appreciated that the function need not be linear. In a specific implementation, the function is simply a difference between the values. It will be appreciated that the function of the two values can be provided directly to the predictive model 78 as a predictor or indirectly by providing both values to the predictive model as predictors, with the predictive model generating the function inherently (e.g., as the linear combination in the model produced by a regression, as a combined feature in a hidden later of a neural network, etc.). The inventors have determined that the use of pre-intervention and post-intervention predictors allows for the effects of the intervention to be captured in the predictive model 74, greatly enhancing the predictive capacity of the model for a given patient. The results of the predictive modeling can be provided to the user interface 74 for display to the user.

Figure 3:
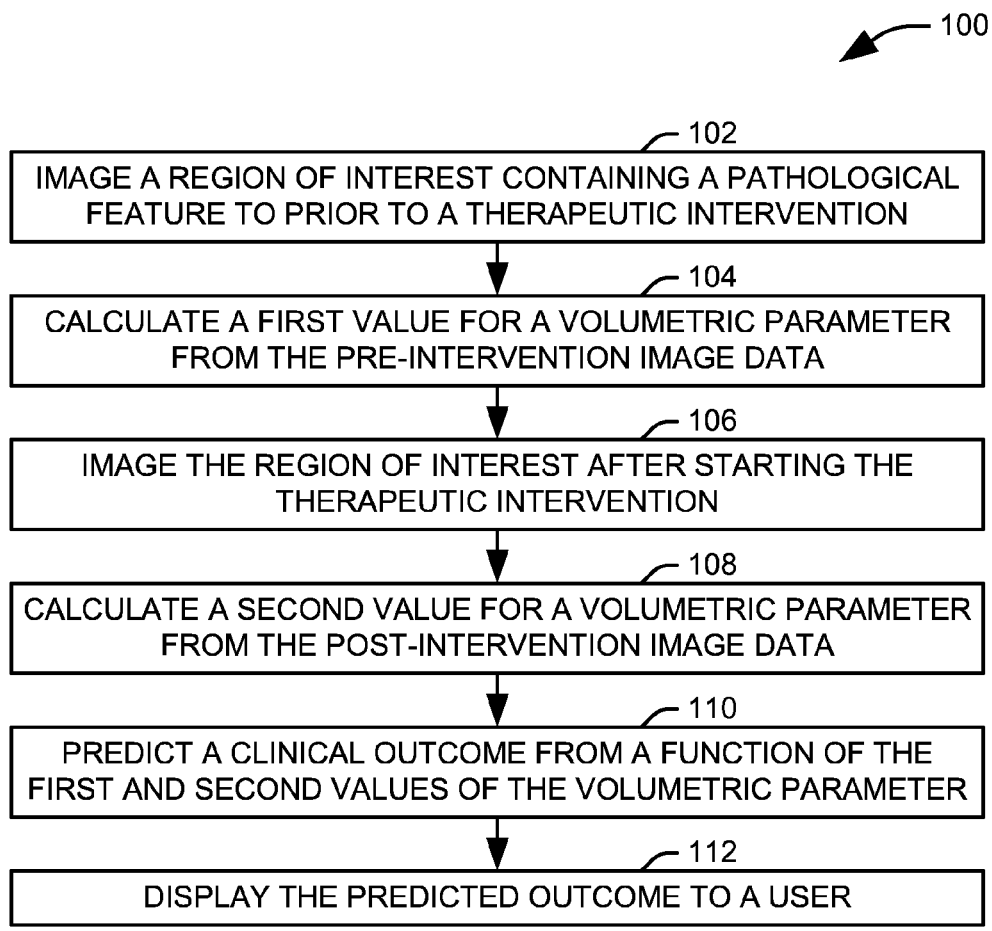
FIG. 3 illustrates a method for predicting a clinical outcome in accordance with an aspect of the present invention.

In view of the foregoing structural and functional features described above, a method in accordance with various aspects of the present invention will be better appreciated with reference to FIG. 3. While, for purposes of simplicity of explanation, the method of FIG. 3 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 3 illustrates a method 100 for predicting a clinical outcome from volumetric data in accordance with an aspect of the present invention. At 102, a region of interest containing a pathological feature is imaged prior to a start of a therapeutic intervention to provide a set of pre-intervention scan data. In one implementation, the imaging is performed on a region of eye tissue using an OCT imager to provide a series of B-scan images. At 104, a first value of a volumetric parameter is calculated from the set of pre-intervention scan data. For example, the volumetric parameter can include one of a total volume, a base area, a top area, a maximal base width, and a minimum width of the volume representing the pathological feature.

In one implementation, the volumetric parameter is determined by segmenting the boundaries of the pathological feature in each of a plurality of images and joining the images into a volume representing the feature. Specifically, determining, for each of a series of images in the pre-intervention scan data, a set of segmentation boundaries within each image representing a cross-section of the pathological feature can be determined and linked with sets of segmentation boundaries from adjacent images in the series to generate a polygonal mesh representing a volumetric reconstruction of the pathological feature. The volumetric parameter is calculated from the generated volumetric reconstruction.

At 106, the region of interest is imaged after the start of the therapeutic intervention to provide a set of post-intervention scan data. At 108, a second value of the volumetric parameter is calculated from the set of post-intervention scan data. It will be appreciated that the second value for the volumetric parameter can be calculated in much the same manner as the first value.

At 110, a clinical outcome associated with the therapeutic intervention as at least a function of the first value of the volumetric parameter and the second value of the volumetric parameter. For example, the clinical outcome can be predicted by providing a plurality of predictors to a predictive model that can utilize an appropriate supervised learning algorithm, such as a regression model, an artificial neural network, a support vector machine, or a statistical classifier. Since the predicted clinical outcome is a function of the first and second values of the volumetric parameter, the plurality of predictors can include either both of the first value of the volumetric parameter and the second value of the volumetric parameter or a function of the two values, such as a weighted linear combination of the values. It will be appreciated that the plurality of predictors can also include biometric parameters representing the patient, such as age or the presence or absence of other conditions, that are not derived from either of the set of pre-intervention scan data and the set of post-intervention scan data. At 112, the predicted clinical outcome is displayed to a user at an associated output device.

In one implementation, the clinical outcome is a minimum length of time for which it is advisable to allow a patient to remain prone after a therapeutic intervention to address a macular hole. Specifically, the intervention can include a vitrectomy and peeling of an internal limiting membrane (ILM). This intervention can be performed using OCT assisted surgery, which allows ready access to images both prior to and immediately after the ILM peeling. In this implementation, the volumetric parameter can include one or both of a volume of a macular hole and a basal diameter of the macular hole. The predictor based on these parameters can represent a change in each parameter after the intervention, such that the predictor is simply the difference between the post-intervention value and the pre-intervention value. The inventors have determined that a change in these values has predictive value in determining how rapidly the macular hole will close once the intervention has been completed.

Figure 4:
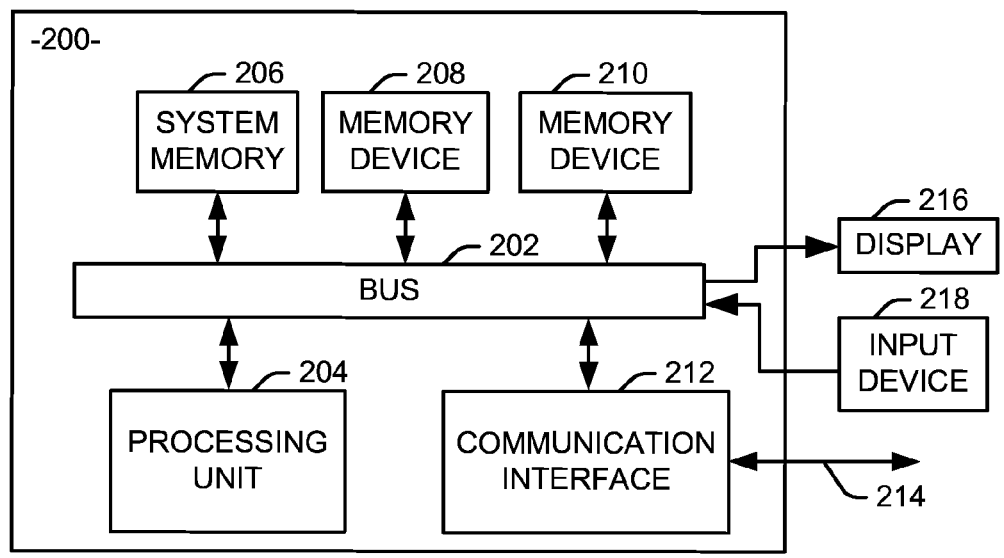
FIG. 4 is a schematic block diagram illustrating an exemplary system of hardware components capable of implementing examples of the systems and methods disclosed herein.

FIG. 4 is a schematic block diagram illustrating an exemplary system 200 of hardware components capable of implementing examples of the systems and methods disclosed in FIGS. 1-3, such as the imaging systems illustrated in FIGS. 1 and 2. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an OCT imaging system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

From the above description of the invention, those skilled in the art will perceive improvements, changes, and modifications. Such improvements, changes, and modifications within the skill of the art are intended to be covered by the appended claims.

Having described the invention, we claim:

1. A non-transitory computer readable medium storing executable instructions comprising:
   a coarse segmentation component configured to determine, for each of a series of B-scan images, a set of constraint boundaries, based on natural contours within a region of tissue, from an optical coherence tomography (OCT) B-scan image and truncate all image area outside of the constraint boundaries to provide a truncated image;
   a fine segmentation component configured to determine, for each truncated image, a set of pathology boundaries within the truncated image representing a cross-section of the pathological feature by defining an undirected graph having vertices representing image pixels and edges between the vertices having respective weights defined from a set of at least one image characteristic and find an optimal segmentation for the defined graph;
   a mesh generation component configured to link the sets of pathology boundaries from adjacent images in the series of B-scan images to generate a polygonal mesh representing a volumetric reconstruction of the pathological feature; and a user interface configured to provide the polygonal mesh to an associated display.

2. The non-transitory computer readable medium of claim 1, further comprising a volumetric measurement component configured to calculate volumetric parameters from the volumetric reconstruction representing the pathological feature.

3. The non-transitory computer readable medium of claim 2, further comprising a predictive model configured to predict a clinical outcome for a patient according to a plurality of predictors, the plurality of predictors including at least one volumetric parameter.

4. The non-transitory computer readable medium of claim 2, further comprising a predictive model configured to predict a clinical outcome for a patient according to a plurality of predictors, the plurality of predictors including at least one predictor that is a function of a first volumetric parameter, derived from an OCT scan taken prior to a start of a therapeutic intervention, and a second volumetric parameter, derived from an OCT scan taken after the start of a therapeutic intervention.

5. The non-transitory computer readable medium of claim 1, wherein the set of at least one image characteristic is a first set of at least one image characteristic and the fine segmentation component is configured to define the undirected graph such that each pixel has defined edges to each of a source and a sink vertex, the edges having respective weights based on a second set of at least one image characteristic and find the optimal segmentation for the defined graph as an optimal solution to a maximum-flow, minimum-cut problem defined by the undirected graph.

6. The non-transitory computer readable medium of claim 1, the second set of at least one image characteristic comprising a set of pixel intensity values and histogram similarity metrics representing regions of the image.

7. The non-transitory computer readable medium of claim 1, the set of at least one image characteristic for a given edge comprising a gradient between pixels linked by the edge and a neighborhood similarity metric representing the similarity of pixels connected to a given pixel associated with the edge.

8. A non-transitory computer readable medium storing executable instructions comprising:

a segmentation component configured to determine, for each of a series of images of a region of interest containing a pathological feature, a set of segmentation boundaries within the image representing a cross-section of the pathological feature by defining an undirected graph having vertices representing image pixels and edges between the vertices having respective weights defined from a set of at least one image characteristic and find an optimal segmentation for the defined graph;

a mesh generation component configured to link the sets of segmentation boundaries from adjacent images in the series of images to generate a polygonal mesh representing a volumetric reconstruction of the pathological feature;

a volumetric measurement component configured to calculate volumetric parameters from the volumetric reconstruction representing the pathological feature; and a user interface configured to provide the calculated volumetric parameters to an associated display.

9. The non-transitory computer readable medium of claim 8, further comprising a predictive model configured to predict a clinical outcome for a patient according to a plurality of predictors, the plurality of predictors including at least one of the calculated volumetric parameters.

10. The non-transitory computer readable medium of claim 8, further comprising a predictive model configured to predict a clinical outcome for a patient according to a plurality of predictors, the plurality of predictors including at least one predictor that is a function of a first volumetric parameter, derived from a set of images taken prior to a start of a therapeutic intervention, and a second volumetric parameter, derived from a set of images taken after the start of a therapeutic intervention.

11. A system comprising:

an OCT imager to provide the a series of images of the region of interest;

the non-transitory computer readable medium of claim 8;

a processor operatively connected to the non-transitory computer readable medium; and the display associated with the user interface.

12. A method comprising:

imaging a region of interest containing a pathological feature with an associated imager prior to a start of a therapeutic intervention to provide a set of pre-intervention scan data;

calculating a first value of a volumetric parameter from the set of pre-intervention scan data, wherein calculating a first value of a volumetric parameter from the set of pre-intervention scan data comprises:

determining, for each of a series of images in the pre-intervention scan data, a set of segmentation boundaries within each image representing a cross-section of the pathological feature by defining an undirected graph having vertices representing image pixels and edges between the vertices having respective weights defined from a set of at least one image characteristic and finding an optimal segmentation for the defined graph;

linking the sets of segmentation boundaries from adjacent images in the series of images to generate a polygonal mesh representing a volumetric reconstruction of the pathological feature; and calculating the first value of the volumetric parameter from the volumetric reconstruction representing the pathological feature;

imaging the region of interest with the imager after the start of the therapeutic intervention to provide a set of post-intervention scan data;

calculating a second value of the volumetric parameter from the set of post-intervention scan data;

predicting a clinical outcome associated with the therapeutic intervention as at least a function of the first value of the volumetric parameter and the second value of the volumetric parameter, the clinic outcome comprising a minimum period of time for which it is necessary for the patient to remain in a prone position after the therapeutic intervention; and displaying the predicted clinical outcome to a user at an associated output device.

13. The method of claim 12, wherein imaging the region of interest comprises imaging a region of eye tissue using an OCT imager to provide a series of B-scan images.

14. The method of claim 12, wherein the volumetric parameter can include one of a base area, a top area, a maximal base width, and a minimum width of the volume representing the pathological feature.

15. The method of claim 12, wherein predicting a clinical outcome associated with the therapeutic intervention comprises providing a plurality of predictors to a predictive model, the plurality of predictors including one of the function of the first value of the volumetric parameter and the second value of the volumetric parameter and a set including both of the first value of the volumetric parameter and the second value of the volumetric parameter.

16. The method of claim 15, the plurality of predictors comprising at least one biometric parameter representing the patient that is not derived from either of the set of pre-intervention scan data and the set of post-intervention scan data.

17. The method of claim 12, wherein the volumetric parameter represents one of a volume and a basal diameter.

* * * * *